United States Patent [19]
Wallshein

[11] 4,023,274
[45] * May 17, 1977

[54] ORTHODONTIC SPRING CLIP

[76] Inventor: Melvin Wallshein, 8645 Bay Parkway, Brooklyn, N.Y. 11214

[*] Notice: The portion of the term of this patent subsequent to Mar. 18, 1992, has been disclaimed.

[22] Filed: June 2, 1975

[21] Appl. No.: 583,160

[52] U.S. Cl. .............................................. 32/14 A
[51] Int. Cl.² ......................................... A61C 7/00
[58] Field of Search ................................... 32/14 A

[56] References Cited
UNITED STATES PATENTS

| | | | |
|---|---|---|---|
| 3,091,857 | 6/1963 | Rubin et al. | 32/14 A |
| 3,128,552 | 4/1964 | Broussard | 32/14 A |
| 3,497,954 | 3/1970 | Kesling | 32/14 A |
| 3,729,826 | 5/1973 | Kesling | 32/14 A |
| 3,854,207 | 12/1974 | Wildman | 32/14 A |
| 3,871,096 | 3/1975 | Wallshein | 32/14 A |

Primary Examiner—J.N. Eskovitz
Attorney, Agent, or Firm—Flynn & Frishauf

[57] ABSTRACT

A spring clip for use with an arch wire and an orthodontic bracket includes a collar portion generally in the shape of a loop which is engageable with the orthodontic bracket. The collar portion may be at least partially resilient, or may be deformable to be positively retained with the bracket. A retaining finger, preferably integral with the collar, extends at least partially across the bracket engaging loop defined by the collar. The finger is at least partially and resiliently movable in directions generally transverse to the plane defined by the loop and is arranged to apply forces toward the arch wire relative to the bracket to retain the arch wire relative to the bracket. The finger is placed in a biassing condition when the loop-shaped collar of the orthodontic appliance is engaged onto the bracket.

52 Claims, 21 Drawing Figures

ORTHODONTIC SPRING CLIP

CROSS REFERENCE TO RELATED APPLICATION

U.S. Pat. No. 3,871,096, issued Mar. 18, 1975 to Melvin Wallshein, the contents of which are incorporated herein by reference.

BACKGROUND OF THE INVENTION

The present invention relates to orthodontic spring clips which are to be used in association with an orthodontic bracket and arch wire.

Various orthodontic procedures involve the securing of an orthodontic bracket to a malocculded tooth, the bracket having a channel for receiving an arch wire. In order to properly confine the arch wire within the channel of the bracket, a tie wire, which is generally non-resilient in nature, is utilized. This type of tie wire is disadvantageous as discussed in my prior U.S. Pat. No. 3,871,096.

An object of the present invention is to provide improved orthodontic spring clips which are simple to use and are readily applicable to mass production techniques.

SUMMARY OF THE INVENTION

In accordance with the present invention, an orthodontic spring clip appliance is provided for use with an orthodontic bracket having a front portion and a rear portion of reduced cross-sectional area, the rear portion of the bracket defining at least a portion of at least one channel for receiving at least a portion of the orthodontic spring clip appliance therein. According to a first feature of the invention, the spring clip appliance includes a resilient collar portion generally in the shape of a loop which is adapted to pass over and engage with the orthodontic bracket, and having at least one resiliently displaceable bracket engaging member which is resiliently displaceable to permit the size of the loop to be increased and to thereby permit the loop to be releasably snapped onto the bracket.

According to a further feature of the invention, the resilient collar portion is additionally formed in a curved plane, so that when the loop is deformed into a substantially flat plane, the loop is enlarged to permit the loop to be releasably snapped onto the bracket.

According to a still further feature of the invention, the collar portion is formed of a deformable material, which may or may not also be resilient, and the loop defined by the collar has a dimension substantially corresponding to or larger than the external dimension of the bracket. After passing the loop over the bracket, the loop is deformed to decrease the size thereof, thereby engaging the collar portion with the bracket.

In all three of the above arrangements of the present invention, an elongated finger means in the form of at least one biassing finger extends from the collar portion and has a biassing portion spaced to at least one side of the loop and which is at least partially and resiliently movable in a direction generally transverse to a plane generally defined by the loop. The biassing finger is arranged to apply forces toward the arch wire relative to the bracket to retain the arch wire relative to the bracket. The at least one biassing finger is placed in the biassing condition when the loop-shaped collar is engaged on the bracket.

In a further embodiment of the invention, the bracket includes a channel, which may be on a front portion of the bracket, for engaging a projection or other channel engaging member of the spring clip to retain the spring clip thereon. The spring clip engaging channel may be anywhere on the bracket, depending upon the particular design of the spring clip used therewith.

DETAILED DESCRIPTION OF ILLUSTRATED EMBODIMENTS

Figure 1A:
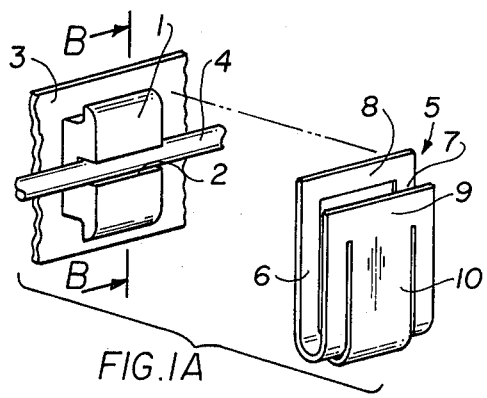
FIG. 1A shows a bracket with an arch wire received in the bracket of the channel, and a perspective view of an orthodontic spring clip according to the present invention.
Figure 1B:
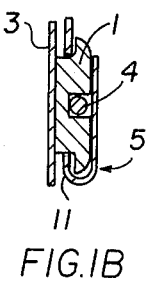
FIG. 1B is a sectional view of the embodiment of FIG. 1A, in the assembled state, taken along the line B—B in FIG. 1A.
Figures 1C, 1D:
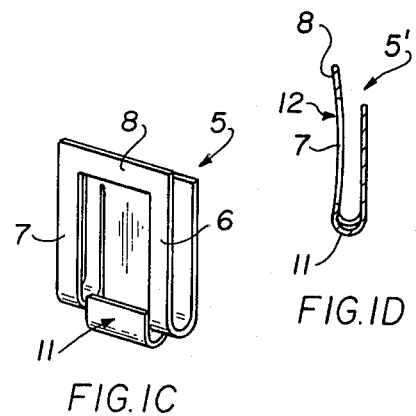
FIG. 1C is a perpespective view of the spring clip of FIG. 1A, but taken from the opposite side.
FIG. 1D is a cross-sectional view of the spring clip of FIGS. 1A–1C wherein a portion thereof is curved in side elevation.

Referring to FIGS. 1A–1C, an orthodonic bracket 1 having an arch wire receiving channel 2 therein is mounted to an orthodonic band 3 which in turn is mounted to a tooth (not shown). Alternatively, the bracket 1 may be directly secured to a tooth. An arch wire 4 is shown received in the channel 2. An orthodontic spring clip 5 is preferably derived from a flat metal stamping of, for example, a springy metal and comprises side frame members with a cross-piece 8 extending therebetween and preferably integral therewith. The side members are spaced apart so that they straddle the sides of the bracket 1 when engages therewith. The spring clip of FIGS. 1A-1C is generally U-shaped in cross-section, and the side members 6 and 7 extend around to form the other leg of the U-shaped configuration. At the other end of side members 6,7 is a cross-portion 9 which is preferably integral with side members 6,7. Extending from cross-member 9, and between side members 6 and 7 is a central portion 10 which curves around the bottom of the U-shaped configuration, the free end of which forms a clip portion 11. Slots are defined between the central member 10 and the side members 6,7 preferably along a substantial portion of the central member as shown in FIGS. 1A and 1C.

In operation, the spring clip of FIGS. 1A of 1C is first engaged with the bracket, the engagement being facilitated by means of the springiness of the metal so that the clip portion 11 can be deformed to permit the spring clip to engage the bracket, the spring clip portion 11 then springing back to its initial position so as to lock the spring clip on the bracket 1 behind the flanges of the bracket as clearly seen in FIG. 1B. Then, the arch wire is installed by flexing, for example, the free portion 9,10 away from the bracket so that the arch wire may be passed between the bracket and the portions 9,10 of the spring clip. When the arch wire 4 becomes fully received in the channel 2, the free portion of the spring clip will "spring" to its initial position to effectively lock the arch wire 4 in the channel 2, as should be apparent from FIG. 1B.

As shown in FIG. 1D, the portion of the spring clip 12 closest to the surface of the tooth is curved in side elevation. In this construction, additional clearance to facilitate passing the clip over the orthodontic bracket 1 can be obtained by straightening the curvature of the portion 12 of the clip 5' so as to essentially elongate the opening defined between clip portion 11 and top cross piece 8. In this embodiment, if the curvature of the portion 12 is sufficient, straightening thereof may provide sufficient clearance so that the clip portion 11 need not be flexed when the spring clip is installed on an orthodontic bracket. However, preferably, the clip portion 11 is fabricated so that it must be flexed in installing the bracket on the tooth. This provides firmer engagement of the clip with the bracket when the clip portion 11 returns to its original un-sprung position.

Figures 2A, 6:
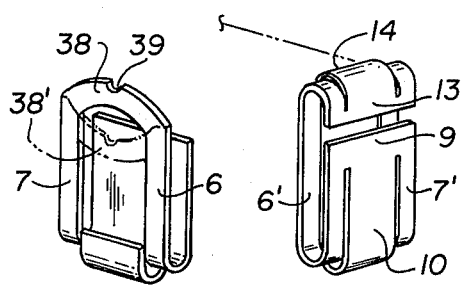
FIG. 2A is a perpespective view of a further embodiment of a spring clip according to the present invention.
FIG. 6 is a rear perspective view of a further embodiment of the present invention.
Figure 2B:
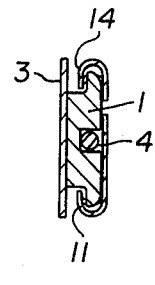
FIG. 2B is a cross-sectional view of the spring clip of FIG. 2A assembled on an orthodonic bracket.
Figure 2C:
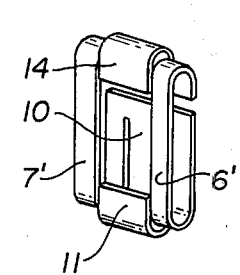
FIG. 2C is a perspective view of the spring clip of FIG. 2A taken from the opposite side.

A further embodiment of the present invention is illustrated in FIGS. 2A-2C, similar reference numerals being used for corresponding elements in FIGS. 1A-1C. In the embodiment of FIGS. 2A-2B, an additional clip portion 14 extends from an end cross-piece 13, slots being provided between the clip portion 14 and the side members 6',7' to enable the clip portion 14 to flex independently of the side members, similar to clip portion 11 described above. FIGS. 2B illustrates the spring clip of FIG. 2A engaged with a bracket 1, the clip portions 11 and 14 being engaged behind the flanges of the bracket 1. In operation, the spring clip is first engaged with a bracket 1 and then an arch wire 4 is installed in the same manner as discussed above with respect to FIGS. 1A-1C.

Figure 2D:
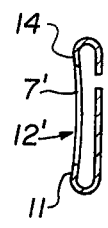
FIG. 2D is a cross-sectional view of the spring clip of FIGS. 2A–2C wherein a portion thereof is curved in side elevation.

FIG. 2D shows a similar embodiment to FIGS. 2A-2C, except that the portion 12' is curved in side elevation as illustrated. As with respect to FIG. 1D, if the curvature of portion 12' is sufficient, little flexing of clip portions 11 and 14, if at all, is required. By straightening the curved portion 12, sufficient clearance can be obtained to install the spring clip over the bracket 1 without flexing clip portions 11 and 14. This, of course depends upon the degree of curvature and the dimensions of the various portions of the clip, as should apparent.

Figure 3A:
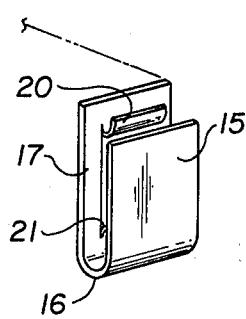
FIG. 3A is a perspective view of a further embodiment of a spring clip according to the present invention.
Figure 3B:
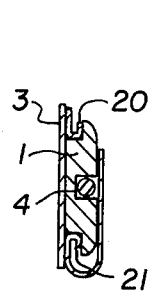
FIG. 3B is a cross-sectional view of the spring clip of FIG. 3A assembled on an orthodontic bracket.
Figure 3C:
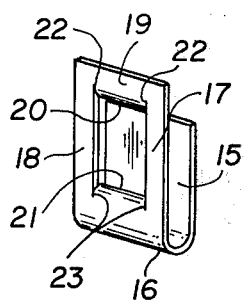
FIG. 3C is a perspective view of the spring clip of FIG. 3A taken from the opposite side.

FIGS. 3A-3C illustrate a further embodiment of the invention wherein the spring clip comprises a front solid portion 15, and a solid portion at the bottom or curved portion 16 of the device in cross-section. Extending from the bottom portion 16 are side members 17 and 18 and a top cross-piece 19 extending therebetween. Turned up clip portions 20 and 21 extend from and are integral with members 19 and 16, respectively, and are designated so as to permit flexure thereof when pressing the clip over the bracket ot engage the portions 20 and 21 behind the flanges of the bracket. This is achieved, for example, by providing short slot portions 22 for the clip portion 20 and short slot portions 23 for the clip portion 21.

Figure 3D:
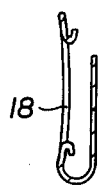
FIG. 3D is a cross-sectional view of the spring clip of FIGS. 3A–3C wherein a portion thereof is curved in side elevation.

As shown in FIG. 3D, the rear portion of the spring clip may be curved, similar to the embodiments of FIGS. 1D and 2D, in which case flexing of clip portions 20 and 21 may not be necessary, depending upon the dimensions and degree of curvature imparted to the clip.

Figure 4A:
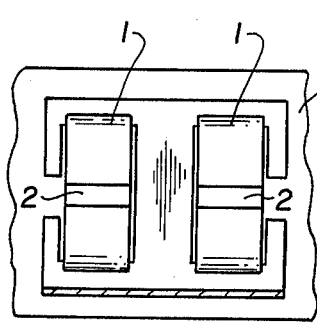
FIG. 4A is a partial view of an embodiment of the present invention for use with twin mounted orthodontic brackets.
Figure 4B:
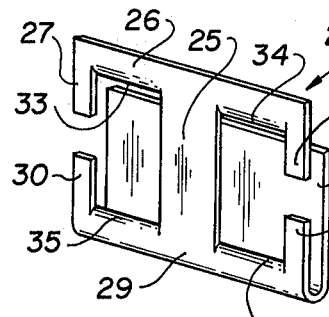
FIG. 4B is a rear perspective view of the spring clip partially shown in FIG. 4A.
Figure 5:
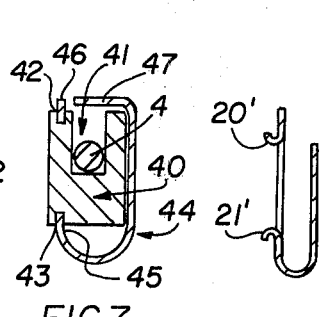
FIG. 5 is a sectional view of an embodiment of the present invention similar to that of FIGS. 3A–3C, but modified.

FIGS. 4A and 4D illustrate a dual type of spring clip according to the present invention for use with twin brackets which are located adjacent each other. FIG. 4A shows a pair of brackets 1 which are mounted, for example, to a band 3. An orthodontic bracket 24, illustrated in detail in FIG. 4B, is engaged over the flanges of the brackets 1 in substantially the same manner as in the embodiment of FIG. 3B. In FIG. 4A, only the rear portion of the bracket 24, that is, the portion closest to the tooth, is shown for clarity of illustration. Referring more particularly to FIGS. 4A and 4B, the portion of the clip 24 closest to the tooth comprises, for example, a central portion 25 and a cross-piece 26 preferably integral with portion 25 having downwardly extending side members 27, 28. A portion 29 extends from the lower part of central member 25, the portion 29 having upwardly extending side members 30, 31. The portion 29 extends around to form the bottom of a U in the cross-section and is integral with a front member 32 which is similar to member 15 of FIGS. 3A and 3C. Member 32 is not shown in FIG. 4A for clarity. Member 26 has a pair of clip portions 33,34, which are similar to clip portions 20,21 of FIGS. 3A-3C. Member 29 has a pair of clip portions 35,36 similar to clip portions 33,34, extending therefrom. The clip portions 33-36 operate similarly to those of FIGS. 3A-3C as should be apparent. In order to provide somewhat more flexibility of the overall structure, and to facilitate engagement thereof with a twin bracket, side members 30 and 27 have a space therebetween, and side members 28,31 have a space therebetween. If desired, these side members may be joined. It should be clear that the rear part of the spring clip 24 may be curved, similar to the embodiments of FIGS. 1D, 2D and 3D, to provide the operational features of these Figures FIG. 5 illustrates another embodiment of the present invention, similar to the embodiment of FIGS. 3A -3C, except that clip portions 20',21', which are similar to clip portions 20 and 21, extend in the opposite direction. In certain applications, this construction may be preferable.

In the embodiment of FIGS. 3A–3D, the up-turned clip portions 20 and 21, which as should be apparent are preferably of resilient spring-type metallic material, provide an additional advantage of wedging or locking the spring clip in place behind the flanges of the bracket 1. Similar wedging or locking effects are achieved by clips 33–36 of FIGS. 4A and 4B and by clips 20' and 21' of FIG. 5.

As discussed hereinabove, the spring clip of the present invention is preferably made of a single stamping of a resilient, springy metallic material. Other materials, such as plastics, may be used. Additionally, the spring clip may be fabricated of materials which are not springy. In this event, for example referring to FIG. 1C, the opening defined between the free edge of the clip portion 11 and the top cross-piece 8 must be large enough so that the clip may pass over the flanges of the bracket 1. After passing the clip over the bracket, a pair of pliers, or the like, may be used to crimp or otherwise deform the clip portion 11 and/or the top cross-piece 8 so as to cause these members to engage behind the flanges of the bracket 1. After deformation of such a non-springy clip having a larger opening than the height of the bracket, the resulting structure looks substantially the same as the mounted spring clip illustrated in FIG. 1B.

Likewise, the embodiment of FIGS. 2A–2D could be fabricated such that the opening defined between the free ends of the clip portions 11 and 14 is larger than the height of the bracket 1 so that it may pass thereover without requiring to be flexed. After passing the clip over the bracket, the clip portions 11 and 14 may then be deformed or bent downwardly by means of pliers, or the like, so as to firmly engage behind the flanges of the bracket 1, the resulting structure being similar to that shown in FIG. 2B.

The embodiment of FIGS. 3A–3D may also be fabricated to have a larger opening than the height of the bracket. However, deformation of the structure of FIG. 3 to provide firm locking to the bracket 1 without excessive distortion of the remainder of the spring clip is not as convenient. In this connection, the embodiments of FIGS. 1A–1D and 2A–2D are more convenient for a crimpable type of spring clip since crimping the upper and lower portions does not substantially affect the side legs 6,7 of the spring clip, so the crimped spring clip is not excessively deformed and retains tight engagement with the bracket 1.

In the embodiments wherein the clip portions are non-resilient and are bendable or crimpable to engage behind the flanges of the bracket, the front or finger portion, for example portion 10 in FIGS. 1A–1C still must be resilient so that the arch wire 4 may be properly retained in the channel 2 of the bracket 1. This is because the front or finger portion of the clip must be bendably displaced when inserting or removing an arch wire and it must then spring back to position against the front of the bracket. Thus, the front or "finger" portion of the clip retains the arch wire in the channel by being self-biassed toward the front surface of the bracket 1. For example, the above-described spring clip may comprise a non-spring type rear or loop section made of deformable material connected to a spring-type front or finger section made of a springy or resilient material which is self-biassed toward the arch wire channel to retain the arch wire in place.

In order to facilitate deformation of a non-spring type of clip, the clip of FIG. 1C, for example, could be formed with an upwardly bowed top cross-piece 38 as illustrated in FIG. 6. This arrangement, wherein the top cross-piece 38 is of non-springy but deformable material, facilitates crimping down of the upper cross-piece 38. In the embodiment of FIG. 1C, when crimping down the top cross-piece 8, the upper portions of the side members 6,7 tend to be drawn together by the effective shortening of the distance therebetween at the portions where side members meet top cross-piece 8. By providing the upwardly bowed top cross-piece 38 as shown in FIG. 6, when cross-piece 38 is deformed downwardly to substantially the position shown in dashed lines in FIG. 6, to engage behind the flanges of a bracket 1, the distance between the side members 6,7 remains substantially the same. Thus, by crimping down the top cross-piece 38, the remainder of the clip is not excessively and disadvantageously deformed, and the clip is held in firm engagement with the bracket 1. A notch 39 is provided in the top cross-piece 38 to facilitate engagement with pliers, or the like, for crimping or deforming the clip.

Figure 7:
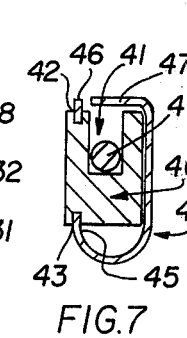
FIG. 7 is a cross-sectional view of a still further embodiment of the present invention.

FIG. 7 illustrates a further embodiment of the invention for use with a bracket 40 defining an arch wire receiving channel 41 and having clip receiving notches 42,43 therein. The spring clip 44 has an upper cross-piece similar to member 8 of FIG. 1C and a lower resilient clip portion 45 similar to clip portion 11 of FIG. 1C. Lower clip portion 45 yields to increase the size of the opening when the spring clip is placed over the bracket 40. When the spring clip is fully received on the bracket 40, the upper cross-piece 46 thereof engages in th upper notch 42 and the lower clip portion 45 engages in a spring-type manner with lower notch 43. The spring clip 44 has an upper finger portion 47 which effectively closes the channel 41 to retain the arch wire 4 therein. In many instances two arch wires are received in channel 41 and the finger 47 effectively retains them in the channel.

While the embodiment of FIG. 7 is described as being similar to the embodiment of FIG. 1C with respect to the manner in which it clips onto a bracket, it should be clear that the engaging members may be provided in pairs, for example as shown in FIG. 2A–2C and/or FIG. 3A–3C. It should be clear that in the various illustrated embodiments of the invention, the engaging portions may be combined in any desired manner — that is, for example, the bracket of FIG. 1C may include the illustrated spring clip portion 11, and the top cross-piece 8 may have a clip portion such as clip portion 20 of FIG. 3A and 3C depending therefrom. Other variations may be made as should be apparent to one ordinarily skilled in the art.

The bracket of FIGS. 1A and 4A are shown as having single slots or channels 2 therein for receiving an arch wire. It should be clear that more than one slot may be provided in the face of the bracket to receive respective arch wires, or a single slot may be large enough to receive more than one arch wire. In any event, the springy finger or front portion of the spring clip which engages the front face of the bracket 1 is of sufficient dimension that it retains the arch wires in their respective slots or channels.

While the front finger 15 of the embodiment of FIG. 3A is shown as being solid, it should be clear that it may have cut-out portion therein or it may take any other desired configuration. In any configuration, however, the front finger should extend sufficiently to retain an arch wire in a slot or channel in the bracket.

Figure 8:
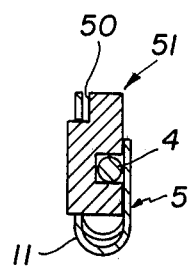
FIG. 8 is a cross-sectional view of a still further embodiment of the present invention.

FIG. 8 illustrates a still further embodiment of the present invention wherein a spring clip arrangement, substantially the same, for example, as the spring clip of FIGS. 1A–1C, is engaged with an upper channel 50 of a bracket 51. The bracket 51 does not have a channel forming means in the lower surface thereof, the spring effect of the spring clip portion 11 providing sufficient frictional effects against the bottom surface of channel 51 to provide secure engagement of the spring clip device 5 with the bracket 51. It should be clear that other types of spring clips, for example the other types shown in the drawings, could be used with bracket 51 or other brackets having similar structural characteristics.

Figure 9:
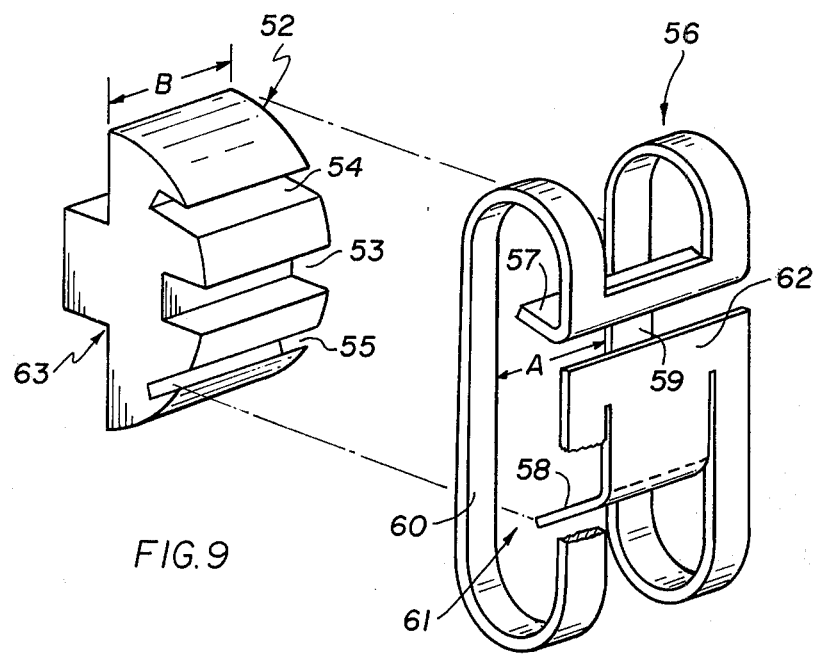
FIG. 9 illustrates a still further embodiment of the present invention.

FIG. 9 illustrates yet another embodiment of the present invention wherein a bracket 52 has an arch wire receiving channel 53 therein and additionally has spring clip receiving channels 54, 55 formed therein. Preferably, the channels 54, 55 are inclined relative to the horizontal as illustrated in FIG. 9. The spring clip useful with the bracket 52, and generally designated by the reference numeral 56 is generally part circular or part oval in shape and has an upper spring clip retaining projection 57 which is adapted to engage with channel 54 and a lower spring clip retaining projection 58 which is adapted to engage with channel 55. The spring clip 56 is made of a springy material, such as spring metal or an appropriate plastic material, and is formed of two legs 59,60 with a void space 61 therebetween. The width of the void space, denoted by the dimension A in FIG. 9, is at least wide enough so that the leg portions 59,60 pass over the sides of the bracket 52. That is, the dimension A in FIG. 9 is at least as great as the dimension B in FIG. 9.

In the illustrated embodiment, the vertical distance between the projections 57 and 58 is greater than the vertical distance between the slots of channels 54,55. Thus, after passing the legs 59,60 over the sides of the bracket, the spring clip is squeezed together so as to bring the projections 57,58 closer to each other and into engagement with the angled channels 54, 55. Then, after engagement, the squeezing pressure on the spring clip is released and the projections 57,58 effectively lock into the channels 54, 55, respectively. The spring clip further has a finger portion 52 above the projection 58, the finger portion 62 being of resilient material and spanning at least a portion of the opening defined by channel 53 so as to effectively retain an arch wire in the channel 53.

It should be clear that the spring clip of FIG. 9 can be made so that the projections 57,58 are closer together than the channels 54,55, in the relaxed state. In this case, a spreading apart force is applied to the spring clip to engage the projections 57,58 with the respective channels 54,55.

The embodiment of FIG. 9 may be further modified to incorporate a lower engaging member which would engage, for example, with a channel 63 defined in part by the bracket 52 rather than engaging with channel 55. Such a bracket would then preferably include an upper projection, similar to projection 57, for engaging a channel such as channel 54. In this instance, the lower channel 55 would not be necessary.

Figures 10A, 10B:
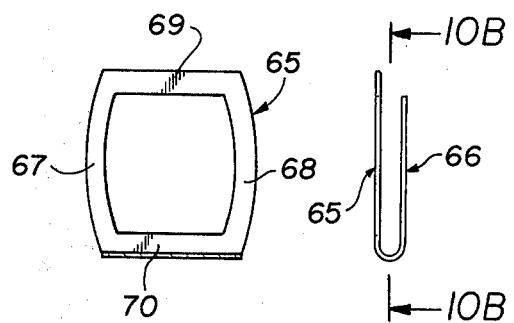
FIG. 10 illustrates yet another embodiment of the present invention.

FIGS. 10A and 10B illustrate still another embodiment of a spring clip utilizing concepts of the present invention. The spring clip of FIGS. 10A and 10B comprises a collar portion 65 with a resilient finger portion 66 coupled thereto as shown in FIG. 10A which is a side view of the spring clip device. FIG. 10B is a front view of the spring clip device with the finger portion omitted for ease of illustration. In operation, the spring clip device of FIGS. 10A and 10B is used with, for example a bracket such as bracket 1 illustrated in FIG. 1A. The collar portion 65 is also of resilient material. The sides 67 and 68 are squeezed inwardly so as to effectively straighten sides 67,68, thus increasing the vertical distance between top portion 69 and bottom portion 70. In this squeeze-in condition, the spring clip is placed over the bracket 1. The pressure is then released from sides 67,68, thereby allowing top and bottom 69,70, respectively, to resume their original relaxed position whereby the distance between them reduces so as to effectively lock the spring clip behind the flanges formed by the bracket 1 in cooperation with either a tooth or a band 3. Alternatively, the collar 65 could be placed over any of the other brackets according to the present invention which have channel defining means for engagement with the collar. The finger 66 is of resilient material and serves the same function as the fingers of the other embodiments discussed hereinabove.

In most of the figures, the bracket 1 is shown having flanges which define spring clip receiving channels between the inner wall of the flange and the surface of the orthodontic band 3 to which the bracket is attached. It should be clear, however, that in cases where the bracket is secured directly to a tooth, the channel may be formed between the inner wall of the flange and the face of the tooth to which it is secured. In other instances, the bracket itself may have a spring clip retaining channel or notch formed directly therein, such as notches 42 and 43 in the embodiment of FIG. 7.

The spring clip device according to the present invention may be made of springy material, or may be made of a resilient plastic material. In the case of fabricating the device out of a springy metal material, the device is preferably stamped from a single stamping and then appropriately bent. In the case of plastics, the device is molded in a conventional manner. As discussed hereinabove, the collar portion may be made of deformable material which is non-resilient, and the finger portion may be the only resilient portion of the device.

As used herein and in the claims appended hereto, the channel receiving the spring clip may be coextensive with the width of the bracket, or may be in the form of a notch, depression or other equivalent clip receiving means. More particularly, referring to FIG. 1A, the portion of the spring clip 8 may have a downwardly extending projection thereon, and the channel defined between the upper front portion of the bracket 1 and the band 3 may extend only partially across the bracket 1 in the direction of the arch wire 4. In this event, the downwardly extending projection of the portion 8 of the spring clip would be receivable in the resulting notch or depression formed in the rear portion of the bracket 1. Such a modification should be apparent to those ordinarily skilled in the art.

Still further, the bracket need not necessarily have a channel for receiving the arch wire 4 therein. The channel may be formed in the finger portion or arch wire retaining portion of the spring clip 7. Alternatively, the channel may be partially formed in the bracket 1 and partially formed in the arch wire retaining finger so that the two channel portions cooperate to receive and engage an arch wire 4.

I claim:

1. An orthodontic spring clip appliance for use with an orthodontic arch wire and with an orthodontic bracket having a front portion and an engaging channel defining portions, said bracket being connectable to a tooth by means of, for example, an orthodontic band, said arch wire extending proximate said bracket, and said channel defining portion of said bracket defining at least a portion of at least one channel for receiving at least a portion of the orthodontic spring clip appliance therein, said spring clip appliance comprising:

a resilient collar portion generally in the shape of a loop and having at least one resiliently displaceable bracket engaging member, said loop-shaped collar having dimensions substantially corresponding to the external dimensions of the portion of the bracket which defines at least a portion of said at least one channel and being made at least partially of a resilient material to permit resilient displacement of said at least one bracket engaging member to increase the size of said loop to thereby permit said loop-shaped collar to be releasably snapped onto said bracket with at least a portion of said loop-shaped collar at least partially received within said at least one channel; and elongated finger means in the form of at least one biassing finger extending from said collar portion and having a biassing portion spaced to at least one side of said loop and being at least partially and resiliently movable in directions generally transverse to a plane generally defined by said loop and arranged to apply forces toward the arch wire relative to said bracket to retain said arch wire relative to said bracket, whereby said at least one biassing finger is placed in a condition, when said loop-shaped collar is snapped onto said bracket, to apply said retention forces to said arch wire.

2. An orthodontic appliance according to claim 1 for use with said bracket having a front portion which defines an arch wire receiving channel therein, wherein said biassing finger extends from said collar portion and is adapted to extend across at least a portion of said arch wire receiving channel to apply said forces toward said surface of said bracket defining said arch wire receiving channel to retain said arch wire within said arch wire receiving channel.

3. An orthodontic appliance according to claim 2 wherein said biassing finger is arranged to apply forces to an arch wire relative to said bracket when the arch wire moves out of said arch wire receiving channel to thereby retain the arch wire within said arch wire receiving channel.

4. An orthodontic appliance according to claim 1 wherein said spring clip is fabricated from a resilient plastic material.

5. An orthodontic appliance according to claim 1 wherein said biassing finger extends substantially entirely across said loop and is substantially parallel to a plane generally defined by said loop.

6. An orthodontic appliance according to claim 1 wherein said loop is generally of rectangular configuration.

7. An orthodontic appliance according to claim 1 wherein said collar and finger means are constructed from a one-piece metal stamping.

8. An orthodontic appliance according to claim 1 wherein said collar portion and said finger form a generally U-shape in a plane perpendicular to the plane generally defined by said loop.

9. An orthodontic appliance according to claim 1 wherein said generally loop-shaped collar has at least one opening in said loop.

10. An orthodontic appliance according to claim 1 wherein said generally loop-shaped collar defines a closed loop.

11. An orthodontic appliance according to claim 1 wherein said resiliently displaceable bracket engaging member comprises a resilient spring-clip portion defining at least a portion of said loop and which is displaceable relative to the remaining portions of said collar defining the remainder of said loop.

12. An orthodontic appliance according to claim 11 wherein said resiliently displaceable bracket engaging member resiliently extends from said finger means.

13. An orthodontic appliance according to claim 11 wherein said loop is generally of rectangular configuration, and wherein said resilient spring-clip portion defines at least one side of said rectangular configuration, said at least one side being displaceable relative to the remaining portions of said loop, and said at least one channel is defined at least partly by a rear portion of said bracket which has a reduced cross-sectional area as compared to said front portion.

14. An orthodontic appliance according to claim 13 comprising at least a second resiliently displaceable bracket engaging member defining at least a second side of said loop, said second side being opposite said first side, said second side being displaceable relative to the remaining portions of said loop.

15. An orthodontic appliance according to claim 14 wherein said spring-clip portions extend around said bracket to a position proximate the front surface of said bracket and are displaceable relative to the remaining portions of said spring-clip appliance over a substantial portion thereof.

16. An orthodontic appliance according to claim 1 wherein said resilient collar portion defines at least two spaced loops, each loop having at least one resiliently displaceable bracket engaging member, each of said loops being releasably snappable onto the rear portion of respective brackets.

17. An orthodontic appliance according to claim 16 wherein said elongated finger means comprises portions arranged to apply forces toward each of said respective brackets.

18. An orthodontic appliance according to claim 16 wherein said collar and finger means are constructed from a one piece metal stamping.

19. An orthodontic appliance according to claim 1 for use with said bracket which is connected to a tooth by means of an orthodontic band, said at least one channel being jointly formed by said band and a rear reduced cross-sectional area portion of said bracket, said resilient collar portion of said spring clip appliance including means adapted to be engaged in said at least one channel formed by said band and said rear reduced cross-sectional area portion of said bracket.

20. An orthodontic appliance according to claim 1 for use with said bracket which completely defines said at least one channel, and said resilient collar portion of said spring clip appliance including means adapted to be at least partially engaged in said at least one channel.

21. An orthodontic appliance according to claim 1 wherein said resiliently displaceable bracket engaging member comprises a turned-back extension of at least a portion of said loop and which is resiliently displaceable relative to the remaining portions of said loop for increasing the dimensions of said loop.

22. An orthodontic appliance according to claim 21 wherein said turned-back portion is integral with said collar and is bent back toward itself in a direction away from said biassing finger.

23. An orthodontic appliance according to claim 21 wherein said turned-back portion is integral with said collar and is bent back toward itself in a direction toward said biassing finger.

24. An orthodontic appliance according to claim 1 wherein said resilient collar portion is substantially flat so that said loop is in a substantially flat plane.

25. An orthodontic appliance according to claim 1 wherein said collar is generally in the shape of a resilient loop formed in a curved plane, said loop having dimensions when curved substantially corresponding to the external dimensions of the rear portions of the bracket, and said loop having larger dimensions when said loop is deformed into a substantially flat plane, resilient displacement of said at least one bracket engaging member further increasing the size of said loop.

26. An orthodontic appliance according to claim 25 wherein said loop is generally of rectangular configuration.

27. An orthodontic appliance according to claim 25 wherein said collar and finger means are constructed from a one-piece metal stamping of resilient metal.

28. An orthodontic appliance according to claim 25 wherein said resiliently displaceable bracket engaging member comprises a resilient spring-clip portion defining at least a portion of said loop and which is displaceable relative to the remaining portions of said collar defining the remainder of said loop.

29. An orthodontic appliance according to claim 28 wherein said resiliently displaceable bracket engaging member resiliently extends from said finger means.

30. An orthodontic appliance according to claim 28 wherein said loop is generally of rectangular configuration, and wherein said resilient spring-clip portion defines at least one side of said rectangular configuration, said at least one side being displaceable relative to the remaining portions of said loop, and said at least one channel is defined at least partly by a rear portion of said bracket which has a reduced cross-sectional area as compared to said front portion.

31. An orthodontic appliance according to claim 25 for use with said bracket which is connected to a tooth by means of an orthodontic band, said at least one channel being jointly formed by said band and a rear reduced cross-sectional area portion of said bracket, said resilient collar portion of said spring clip appliance including means adapted to be engaged in said at least one channel formed by said band and said rear reduced cross-sectional area portion of said bracket.

32. An orthodontic appliance according to claim 25 for use with said bracket which completely defines said at least one channel, and said resilient collar portion of said spring clip appliance including means adapted to be at least partially engaged in said at least one channel.

33. An orthodontic appliance according to claim 25 wherein said resiliently displaceable bracket engaging member comprises a turned-back extension of at least a portion of said loop and which is resiliently displaceable relative to the remaining portions of said loop for increasing the dimensions of said loop.

34. An orthodontic appliance according to claim 1 for use with a bracket which defines at least one engaging channel in a front portion thereof for receiving at least a portion of said loop-shaped collar, wherein said collar portion is in a substantially curved plane and is adapted to curve around at least a portion of said bracket.

35. An orthodontic appliance according to claim 34 wherein said at least one resiliently displaceable bracket engaging member is adapted to be received in said engaging channel of said bracket.

36. An orthodontic appliance according to claim 1 wherein said at least one resiliently displaceable bracket engaging resilient collar portion has two opposing bracket engaging sides and two opposing, resilient, outwardly bulged sides which are located spaced from each other and between respective bracket engaging sides, said outwardly bulged sides being adapted to be squeezed inwardly to space said bracket engaging sides apart to increase the dimensions of said collar to enable said collar to be passed over said bracket, said bracket engaging sides moving toward each other when the squeezing forces are released from said outwardly bulged sides, and biassing finger extending from one of said bracket engaging sides.

37. An orthodontic appliance according to claim 25 wherein said spring clip is fabricated from a resilient plastic material.

38. An orthodontic spring clip appliance for use with an orthodontic arch wire and with an orthodontic bracket having a front portion and an engaging channel defining portion, said bracket being connectable to a tooth by means of, for example, an orthodontic band, said arch wire extending proximate said bracket, and said channel defining portion of said bracket defining at least a portion of at least one channel for receiving at least a portion of the orthodontic spring clip appliance therein, said spring clip appliance comprising:

a collar portion generally in the shape of a loop and having at least one displaceable bracket engaging member, said collar defining a loop having a dimension substantially corresponding to or larger than an external dimension of the front portion of the bracket and being made of a deformable material to permit displacement of said at least one bracket and engaging member to decrease the size of said loop after passing over the front portion of the bracket to thereby positively engage said loop-shaped collar onto the channel defining portion of said bracket with at least a portion of said loop-shaped collar at least partially received within said at least one channel; and elongated finger means in the form of at least one biassing finger extending from said loop and having a biassing portion spaced to at least one side of said loop and being at least partially and resiliently movable in directions generally transverse to the plane defined by said loop and arranged to apply forces toward a surface of said bracket which defines said arch wire receiving channel means to retain the arch wire relative to said bracket, whereby said at least one biassing finger is placed in a condition, when said loop is engaged onto said bracket, to apply said retention forces to said arch wire.

39. An orthodontic appliance according to claim 38 wherein said loop is generally rectangular, and said at least one displaceable bracket engaging member comprises at least one side of said generally rectangular loop, said at least one side being bulged outwardly in its non-deformed state, and is bulged inwardly of said loop in its deformed state.

40. An orthodontic appliance according to claim 38 further comprising at least one resiliently displaceable bracket engaging member forming at least a portion of said loop, and which is resiliently displaceable, to permit firm engagement of said collar portion to said bracket.

41. An orthodontic appliance according to claim 40 for use with said bracket which defines at least two channels adjacent and relative to said tooth, wherein said deformable bracket engaging member is adapted to be at least partially received in one of said channels and said resilient bracket engaging member is adapted to be at least partially received in the other of said channels when said collar portion is engaged on said bracket.

42. An orthodontic appliance according to claim 38 wherein said displaceable bracket engaging member has means thereon for receiving a tool for deformation thereof.

43. An orthodontic spring clip appliance for use with an orthodontic arch wire and with an orthodontic bracket having a front portion and an engaging channel defining portion, said bracket being connectable to a tooth by means of, for example, an orthodontic band, said arch wire extending proximate said bracket, and said channel defining portion of said bracket defining at least a portion of at least one channel for receiving at least a portion of the orthodontic spring clip appliance therein, said spring clip appliance comprising:

a resilient collar portion generally in the shape of a loop and having at least one displaceable bracket engaging member, said loop-shaped collar having dimensions substantially larger than the maximum external dimensions of the bracket, said loop-shaped collar being formed with a large degree of curvature so that said at least one bracket engaging member curves around in a substantially re-entrant manner so as to define with another fee end portion of said collar an opening smaller than the maximum dimension of said bracket, the curved portion of said resilient collar being passable over said bracket and said collar being resiliently displaceable to permit engagement of said at least one bracket engaging member with an engaging channel of said bracket which is normally displaced therefrom after said spring clip appliance is passed over the front portion of the bracket, whereby in its engaged relaxed state, said bracket engaging member is at least partially engaged with said engaging channel of said bracket; and elongated finger means in the form of at least one biassing finger extending from said collar portion and having a biassing portion spaced to at least one side of a portion of said loop and being at least partially and resiliently movable in directions generally transverse to a plane generally defined by the front of said bracket and arranged to apply forces toward the arch wire relative to said bracket to retain said arch wire relative to said bracket, whereby said at least one biassing finger is placed in a condition, when said loop-shaped collar is engaged with said bracket, to apply said retention forces to said arch wire.

44. An orthodontic appliance according to claim 43 wherein said loop has a rear portion defined by two spaced apart leg portions, which are adapted to straddle the sides of said bracket.

45. An orthodontic appliance according to claim 43 wherein said spring clip is generally C-shaped in cross-section.

46. An orthodontic appliance according to claim 43 wherein said collar and finger means are constructed from a one-piece metal stamping of resilient material.

47. An orthodontic appliance according to claim 43 wherein said collar and finger means are constructed in one-piece from a resilient plastic material.

48. An orthodontic appliance according to claim 43 for use with said bracket which has a pair of spring clip engaging channels on the front portion thereof, wherein said resilient collar portion has a pair of bracket engaging members on opposite sides of said loop and which are resiliently displaceable relative to each other, said bracket engaging members in the relaxed state being spaced apart.

49. An orthodontic appliance according to claim 48 wherein said spring clip has a generally C-shaped cross-section.

50. An orthodontic appliance according to claim 49 wherein the distance between said bracket engaging members is greater than the distance between the engaging channels of a bracket with which it is used.

51. An orthodontic appliance according to claim 44 wherein said at least one bracket engaging member is resiliently displaceable relative to the remainder of said loop.

52. An orthodontic appliance according to claim 49 wherein the distance between said bracket engaging members is different than the distance between the engaging channels of a bracket with which it is used.

* * * * *

UNITED STATES PATENT AND TRADEMARK OFFICE
CERTIFICATE OF CORRECTION

PATENT NO. : 4,023,274
DATED : May 17, 1977
INVENTOR(S) : Melvin WALLSHEIN

It is certified that error appears in the above-identified patent and that said Letters Patent are hereby corrected as shown below:

Column 9, line 7, change "portions" to --portion--;

Column 11, line 22, change "portions" to --portion--;

Column 12, line 16, after "wherein said" delete remainder of the line;

line 17, delete "bracket engaging";

Column 13, line 45, change "fee" to --free--.

Signed and Sealed this nineteenth Day of July 1977

[SEAL]

Attest:

RUTH C. MASON
*Attesting Officer*

C. MARSHALL DANN
*Commissioner of Patents and Trademarks*